(12) United States Patent
Shih et al.

(10) Patent No.: US 8,871,234 B2
(45) Date of Patent: Oct. 28, 2014

(54) UV-RESISTANT GELATIN/SILICA VIRAL PARTICLES, PREPARATION METHOD AND USES THEREOF

(71) Applicant: National Taiwan University, Taipei (TW)

(72) Inventors: Chen Wei Shih, Taipei (TW); Hong-Ping Lin, Taipei (TW); Wen-Jer Wu, Taipei (TW); Shiang-Jiuun Chen, Taipei (TW); Rong-Nan Huang, Taipei (TW)

(73) Assignee: National Taiwan University, Taipei (TW)

( * ) Notice: Subject to any disclaimer, the term of this patent is extended or adjusted under 35 U.S.C. 154(b) by 63 days.

(21) Appl. No.: 13/626,875

(22) Filed: Sep. 25, 2012

(65) Prior Publication Data

US 2014/0086969 A1    Mar. 27, 2014

(51) Int. Cl.
*A01N 63/00*    (2006.01)
*A01P 7/04*    (2006.01)
*A01N 25/26*    (2006.01)

(52) U.S. Cl.
USPC ............................. 424/418; 424/93.6

(58) Field of Classification Search
None
See application file for complete search history.

(56) References Cited

U.S. PATENT DOCUMENTS 5,965,123 A * 10/1999 Ahmed .................. 424/93.2
2010/0119500 A1 * 5/2010 Jokinen et al. .......... 424/94.4
2010/0136657 A1 * 6/2010 Jokinen et al. .......... 435/235.1

FOREIGN PATENT DOCUMENTS

CN        101278680      * 10/2008
JP         07025718       * 1/1995

OTHER PUBLICATIONS

Meunier et al. (Journal of Colloid and Interface Science. 2010; 342: 211-224).*
Machine translation of Cheng et al. (CN 101278680), published Oct. 2006.*
Derwent translation of Fukai et al. (JP 07025718), published Jan. 1995.*
Derwent translation of Ceng et al. CN 101496529, published Aug. 2009.*
"Silica Gels" product overview from Zettachem International Products found at http://linkedin.com/company/zettachem-international/silica-gels-951214/product, downloaded Mar. 13, 2013.*
Royston et al. (Journal of Colloid and Interface Science. 2006; 298: 706-712).*
Okada (Annals of the Phytopathological Society of Japan. 1977; 43 (5): 524-527).*
Stoltze et al. (Zentralbl Veterinarmed B. 1989; 36 (3): 161-167, abstract only).*
Caruso et al. (Chemistry of Materials. 2001; 13 (10): 3272-3282).*

* cited by examiner

*Primary Examiner* — Shanon A Foley
(74) *Attorney, Agent, or Firm* — Chih Feng Yeh; Huntington IP Consulting Co., Ltd

(57) ABSTRACT

Disclosed herein are UV-resistant gelatin/silica coated viral particles, methods for producing the same, and methods for controlling agricultural insect pests using the UV-resistant gelatin/silica coated viral particles.

11 Claims, 1 Drawing Sheet

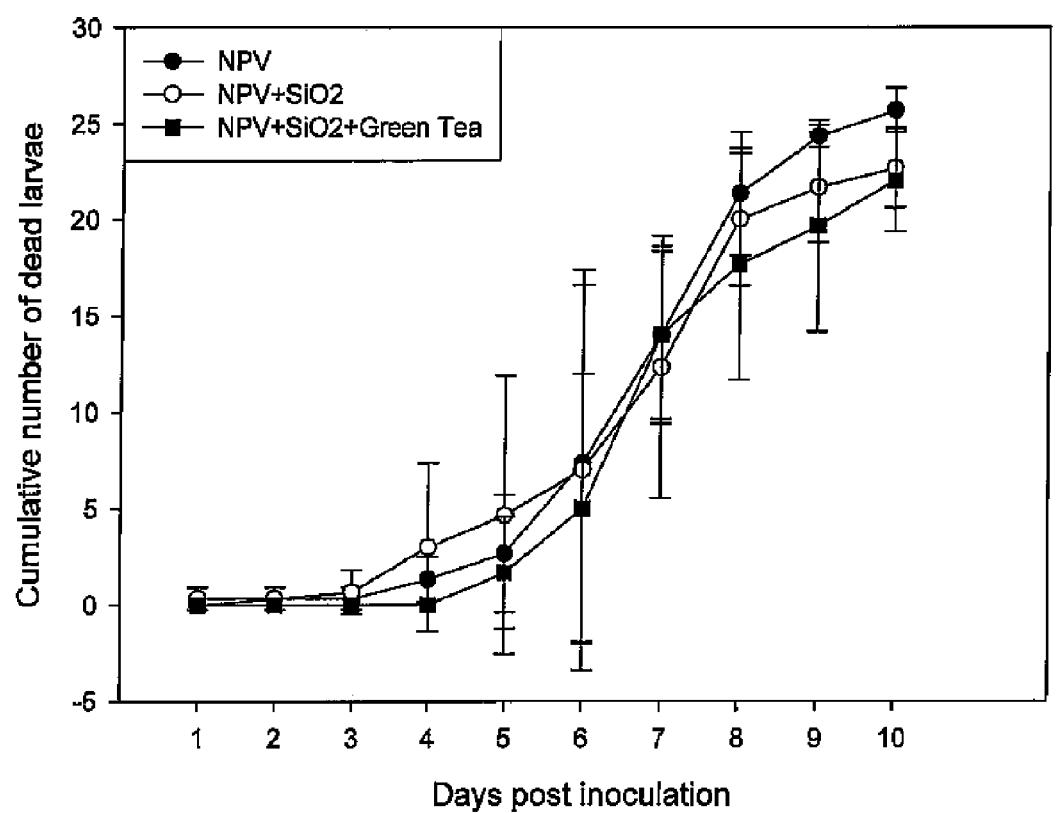

UV-RESISTANT GELATIN/SILICA VIRAL PARTICLES, PREPARATION METHOD AND USES THEREOF

BACKGROUND OF THE INVENTION

1. Technical Field

The present disclosure relates to a UV-resistant gelatin/silica viral particle, preparation method and uses thereof.

2. Description of Related Art

Traditionally pest control has been dominated by the use of chemical insecticides. Although they are fast acting, these chemicals are sometimes environmentally unattractive. In addition, many chemicals used in insect pest control are not species-specific and may affect non-target animals as well as the target pest. Furthermore, these chemicals or their by-products can sometimes persist in the environment for long periods of time.

Biological control, the use of living organisms to control insect pests, has become increasingly more acceptable as a means for controlling pests successfully. For example, the bio-insecticide *Bacillus thuringiensis* (Bt), is used for control of spruce budworm (see U.S. Pat. No. 5,061,489). However, some recent concerns over the specificity of Bt have resulted in the recommendation that it not be used in areas where there are endangered Lepidoptera. Ecological interests have resulted in a shift in emphasis to examine and develop other microbial products, including the insect viruses.

Insect viruses, such as Baculoviruses, are naturally occurring insect pathogens that are considered to be host specific and environmentally safe. They can persist for years to impact on several generations of insects. Baculoviruses are a large group of insect viruses that are known to infect over 500 different insect species, mainly Lepidoptera. Some baculoviruses infect insects which are pests of commercially important agricultural and forestry crops. Such baculoviruses are potentially valuable as biological control agents. There are sixteen countries using baculoviruses to control Lepidoptera and more than 30 species of baculoviruses have been developed as microbial insecticides.

Baculovirus subgroups include nuclear polyhedrosis viruses, now called nucleopolyhedroviruses (NPVs) and granulosis viruses, now called granuloviruses (GVs). In the occluded forms of baculoviruses, the virions (enveloped nucleocapsids) are embedded in a crystalline protein matrix. This structure, referred to as an occlusion body, is the form found extraorganismally in nature, and it is generally responsible for spreading the infection between insects. The characteristic feature of the NPVs is that many virions are embedded in each occlusion body, which is relatively large (up to 5 micrometers). Occlusion bodies of single nucleopolyhedrosis viruses (SNPVs) are smaller and contain a single virion with multiple nucleocapsids each. Multiple nucleopolyedrosis viruses (MNPVs) have multiple nucleocapsids per virion and multiple virions per occlusion body. Granulosis viruses (GVs) have a single virion with one nucleocapsid per occlusion body. In nature, infection is initiated when an insect ingests food contaminated with baculovirus particles, typically in the form of occlusion bodies. The occlusion bodies dissociate under the alkaline conditions of the insect midgut, releasing the virions, which then invade epithelial cells lining the gut. Within a host cell, the baculovirus migrates to the nucleus where replication takes place. Initially, specific viral proteins are produced within the infected cell via the transcription and translation of so-called "early genes." Among other functions, these proteins are required for the replication of the viral DNA, which begins 4 to 6 hours after virus enters the cell. Viral DNA replication proceeds up to about 24 hours post-infection (pi). From about 8 to 24 hours pi, infected cells express "late genes" at high levels. These include components of the nucleocapsid that surround the viral DNA during the formation of progeny virus particles. Production of progeny virus particles begins around 12 hours pi. Initially, progeny viruses migrate to the cell membrane where they acquire an envelope as they bud out from the surface of the cell and are then called budding viruses. The non-occluded, budding viruses can then infect other cells within the insect. Polyhedrin synthesis begins approximately 18 hours after infection and increases to very high levels by 24 to 48 hours pi. At about 24 hrs pi, there is a decrease in the rate of non-occluded viruses production, and most progeny virus particles are then embedded in occlusion bodies. Occlusion body formation continues until the cell dies or lyses. Some baculoviruses infect virtually every tissue in the host insect so that at the end of the infection process, the entire insect is liquified, releasing extremely large numbers of occlusion bodies which can then spread the infection to other insects.

One problem associated with the natural insect virus as insecticide is that the virus tends to degrade over time; or upon being exposed to the nature environment (e.g., sunlight) and thereby loses its capability in infecting insect pests. In view of the forgoing reason, there exists in this art a need for developing an improved insect virus that may withstand UV or sunlight; and a method for prolonging the infectious ability of an insect virus.

SUMMARY

In view of the afore-mentioned problem, a UV-resistant gelatin/silica coated viral particle, a method of producing the same, and a method of controlling agricultural insect pests using the UV-resistant gelatin/silica coated viral particle are disclosed.

The UV-resistant gelatin/silica coated viral particle of the present disclosure is characterized in having a core formed by a plurality of a baculovirus; and a gelatin/silica coating disposed outside the core, in which the gelatin/silica coating has a porosity of about 1.0-10.0 nm, and further includes a green-tea extract absorbed in the porous structure of the gelatin/silica coating outside the core.

The method of producing the UV-resistant gelatin/silica viral particle includes steps of, mixing a gelatin solution with a viral solution to form a first mixture; adding a silica solution into the first mixture to form a precipitate; and immersing the precipitate into a green tea extract for at least 30 min so as to allow the green tea extract to be absorbed by the precipitate and thereby forming the gelatin/silica coated viral particle.

The method of controlling the population of agricultural pests in an agricultural field includes the step of, applying to the agricultural pests or the agricultural field an effective amount of the gelatin/silica viral particle of this disclosure. In one example, the method further includes a step of applying to the agricultural pests or the agricultural field a pest attractant.

These and other features, aspects, and advantages of the present disclosure will become better understood with reference to the following description and appended claims.

BRIEF DESCRIPTION OF THE DRAWINGS

These and other features, aspects and advantages of the present invention will become better understood with reference to the following description, appended claims and the accompanying drawings, where:

FIG. 1 illustrates the respective insecticidal effects of the gelatin/silica viral particle of Example 1, NPV, and NPV coated with silica on insect larvae in accordance with one embodiment of this invention.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

The singular forms "a", "and", and "the" are used herein to include plural referents unless the context clearly dictates otherwise.

The term "portion" is used herein to include weight portion and volume portion unless the context clearly dictates otherwise.

The term "insect" is used herein to include both larval and adult forms of agricultural insect pests that are susceptible to baculoviral infections.

Described herein are UV-resistant gelatin/silica viral particles, preparation methods and uses thereof.

Thus in one aspect, the present invention is related to a UV-resistant gelatin/silica coated viral particle. The UV-resistant gelatin/silica coated viral particle is characterized in having a core structure formed by a plurality of a baculovirus; and a gelatin/silica coating disposed outside the core, in which the gelatin/silica coating has a porosity of about 1.0-10.0 nm, and further includes a green-tea extract, which is absorbed in the porous structure of the gelatin/silica coating outside the core structure of the viral particle of the present disclosure.

The gelatin/silica coated viral particle of the present disclosure may withstand UV irradiation, or is resistant to UV light or sunlight. According to various embodiments of the present disclosure, the gelatin/silica coated viral particle are directly exposed to UV light at a rate of 24,000 µJ/min for at least 90 min, such as 90, 100, 110, 120, 130, 140, 150, 160, 170, 180, 190, and 200 min, before being used as a pesticide. The term "UV-resistant" as used herein means that at least 60% of the gelatin/silica coated viral particle remains active even after UV exposure at a rate of 24,000 µJ/min for at least 90 min.

In another aspect, a method of producing the UV-resistant gelatin/silica coated viral particle is provided. The method includes steps of, mixing a gelatin solution with a viral solution to form a first mixture; adding a silica solution into the first mixture to form a precipitate; and immersing the precipitate into a green tea extract for at least 30 min so as to allow the green tea extract to be absorbed by the precipitate and thereby forming the UV-resistant gelatin/silica coated viral particle.

According to various embodiments of the present disclosure, gelatin and water may be mixed in a ratio from about 1:5 to about 1:200, such as 1:5, 1:10, 1:20, 1:30, 1:40, 1:50, 1:60, 1:70, 1:80, 1:100, 1:110, 1:120, 1:130, 1:40, 1:150, 1:160, 1:170, 1:180, 1:190 and 1:200, so as to produce a gelatin solution. In one specific example, the gelatin solution is obtained by mixing 1 portion of gelatin powder with 5 portions of water and stirred until a clear solution is obtained. Similarly, silica and water may be mixed in a ratio from about 1:8 to about 1:200, such as 1:8, 1:9, 1:10, 1:20, 1:30, 1:40, 1:50, 1:60, 1:70, 1:80, 1:90, 1:100, 1:110, 1:120, 1:130, 1:140, 1:150, 1:160, 1:170, 1:180, 1:190 and 1:200, so as to produce a silica solution. In one specific example, the silica solution is obtained by mixing 1 portion of silica (i.e., $SiO_2$) with 8 portions of water and stirred continuously until a homogeneous solution is obtained; and pH is adjusted to a value of about 3.0 to 7.0, such as 3, 4, 5, 6, or 7; preferably about 5.0. On the other hand, the viral solution is prepared by suspending a baculoviral polyhedral inclusion body (PIB) in a suitable aqueous solution, such as water or an isotonic buffer solution, with a final concentration from about $1\times10^6$ PIB/ml to about $1\times10^9$ PIB/ml; preferably about $1\times10^9$ PIB/m. Suitable baculovirus for use in the present disclosure includes, but is not limited to, the nuclearpolyhedronvirus (NPV), the granulosis virus (GV) or the non-occluded virus. NPV includes *Autographica californica* NPV (AcNPV), *Heliothis zea* NPV (HzNPV), and *Bombyx mori* NPV (Bm-NPV).

According to embodiments of the present disclosure, the gelatin solution is first mixed with the viral solution to form a mixture; the silica solution is then added to the mixture and thereby forming a precipitate. The precipitate may be separated from the rest of the aqueous solution by means known in the art, such as filtration. The precipitate thus formed has a two-layer structure, with an inner core formed by the virus, and a porous coating layer formed by gelatin and silica and is disposed outside the viral core.

The precipitate is then subject to treatment that would extend its shelf life under UV irradiation by immersing the precipitate in a green tea extract for a period of about 30 to 60 min, such as 30, 40, 50 or 60 min, and thereby forming the gelatin/silica viral particle of this invention. The green tea extract may be produced by simmering or dipping 1 portion of a dried green tea leaf in 99 portions of boiled hot water for at least 30 min; after filtering out the green tea leaf, the remaining solution is let stand for at least an hour until it is cool and reaches room temperature. Due to the porous structure of the coating layer of the gelatin/silica viral particle, it is the general belief that the active components in the green tea extract are absorbed therein the coating layer, and thereby rendering the gelatin/silica viral particle with the capability to withstand UV or sunlight; which in term improves the shelf life of the viral particles when used as a pesticide. According to embodiments of the present disclosure, the gelatin/silica coated viral particle may sustain direct exposure to UV light at a rate of 24,000 µJ/min for at least 90 min, such as 90, 100, 110, 120, 130, 140, 150, 160, 170, 180, 190, and 200 min. After being UV irradiated at a rate of 24,000 µJ/min for at least 90 min, at least 60% of the gelatin/silica coated viral particles still remain active.

Accordingly, this invention also provides methods and/or compositions for controlling the population of agricultural pests in an agricultural field.

Compositions in this regard may comprise the UV-resistant gelatin/silica coated viral particle of the present disclosure as the active agent, which may be dispersed in any carrier suitable for agriculture use, such as water, organic solvents, and inorganic carriers. Solid and liquid compositions may be prepared by any conventional procedure which does not affect the viability of the UV-resistant gelatin/silica coated viral particle of the present disclosure. Fundamental formulation processes including dissolving, mixing, milling, granulating, dispersing and etc. Therefore, the present disclosure encompasses composition containing the UV-resistant gelatin/silica coated viral particle as described above, in admixture with agriculturally acceptable excipients including vehicles, carriers, binders, adhesive, humectants, thickeners, dispersing agent, preservatives and insect attractants and etc., as are known in the art. Thus, compositions of the present disclosure may, for example, be formulated as a solid comprising the UV-resistant gelatin/silica coated viral particle, and a finely divided solid carrier. Alternatively, the UV-resistant gelatin/silica coated viral particle may be contained in liquid compositions, including dispersion, emulsion, and suspensions thereof. Any suitable final form of the compositions may be used, including granules, powders, bait pellets (i.e., a solid composition containing the UV-resistant gelatin/silica coated viral particle and an insect attractant or food substance), microcapsules, water dispersible granules, and emulsions. The composition may also include conventional insecticidal agents and/or may be applied in conjunction with conventional insecticidal agents.

The method for controlling the population of agricultural pests in an agricultural field includes steps of, applying to the agricultural pests or the agricultural field an effective amount of the gelatin/silica coated viral particle of the present disclosure or a composition comprising the same. The gelatin/silica coated viral particle may be applied to the agricultural field in any manner which results in the baculovirus coming into contact with the feeding insects to be controlled, or with the particular plant part to be consumed by the insects. For example, in targeting surface leaf-feeding insects, a composition containing the gelatin/silica coated viral particle may be formulated to adhere to leaves (e.g., formulated with adherents) and would be applied in a manner to contact the leaves of the plants (e.g., by spraying). The gelatin/silica coated viral particle of the present disclosure is applied in an amount sufficient to result in baculovirus infection of the target insect when ingested. The present method may be used in addition to or in conjunction with other control measures, such as a second virus, or a pest attractant.

Suitable application methods include, but are not limited to, methods such as dusting or spraying. The gelatin/silica coated viral particle of the present disclosure may be applied as an aerosol, that is, by dispersal in the air by means of a compressed gas such as dichlorodifluoromethane or trichlorofluoromethane. The gelatin/silica coated viral particle may be applied alone or in combination with inert solids such as a dust or suspended in a liquid solution such as organic solvent or an aqueous solution; a surfactant may be added to the solution. Compositions may be applied dry or in the form of a suspension, emulsion or foam. The gelatin/silica coated viral particle is applied to the target insect, or area containing the target insect or parts of plants to be consumed by the target insect, including but not limited to vegetation, fruit, seed, soil or aquatic locales.

The present invention will now be described more specifically with reference to the following embodiments, which are provided for the purpose of demonstration rather than limitation.

EXAMPLES

Example 1

Forming Gelatin/Silica Viral Particles

A gelatin-virus solution was prepared by first dissolving 1 g of gelatin in 5 ml distilled water, then added therein 2 ml of nuclear polyhedron virus ($1 \times 10^9$ PIB/ml), continued stirring the mixture for about 10 min until all the components were mixed homogeneously. A silica solution was prepared by dissolving 5 g of silica in 40 ml distilled water; then adjusted the pH of the solution to be about 5.0. The silica solution was then added to the gelatin-virus solution described above and thereby forming a precipitate, which was separated by vacuum-filtering. A green tea extract was produced by simmering 1 g of green tea leafs in boiled water (about 99 ml) for about 30 min; then filtered out the tea leafs, and let the solution to stand for an hour until it was cool or reached room temperature. The precipitate was then immersed into the thus prepared green tea extract for about 30 min, and thereby forming the gelatin/silica coated viral particles of this invention. The thus produced gelatin/silica viral particle having a green tea extract absorbed therein has a porosity of about 1.0-10.0 nm.

Example 2

Insecticide Activity of the Gelatin/Silica Viral Particles

The insecticidal activity of the gelatin/silica viral particles of Example 1 was tested on insect larvae. The fourth instar *Spodoptera litura* (*S. litura*) larvae (30 larvae per each group) were fasted for 24 hours; then were fed with an artificial diet that was diced into cubes of 0.5 cm$^3$ and pre-treated with 10 µl of the gelatin/silica viral particles of Example 1. In contrast, the control group larvae were fed with an artificial diet that was pre-treated with NPV (i.e., NPV without a gelatin/silica coating, nor with the embedment of 1% green tea extract). The diet in each group was changed every 48 hours, and the number of dead larvae was recorded every 24 hours. Results are illustrated in FIG. 1.

As depicted in FIG. 1, the gelatin/silica viral particles of Example 1 exhibit similar insecticide activity as that of the control NPVs, i.e., NPVs without being coated with gelatin and silica, nor with the embedment of green tea extract. Hence, the results confirm that the insecticide activity of NPVs is not affected by coating the viruses with gelatin and silica.

Example 3

UV Tolerance of the Gelatin/Silica Viral Particle

To test the UV tolerance of the gelatin/silica viral particles, the thus produced gelatin/silica viral particles of Example 1 were first irradiated with UV light for 90 min or 180 min, before being subject to insecticide study of Example 2. As a comparison, NPVs respectively coated with SiO$_2$, TiO$_2$, lignin, and gelatin were also prepared in accordance with similar procedures as described in Example 1; then each of the coated NPVs were exposed to UV light for 90 and 180 min, respectively; before being subject to insecticide study of Example 2. Results are provided in Tables 1 and 2, in which data is presented as the mortality of larvae, and percentage of original activity remaining (OAR %) after UV exposure. OVR (%) is calculated in accordance with equation (1), $$OVR\ (\%) = \frac{NPV\text{-caused larval motality post } UV\ exposure}{NPV\text{-caused larval motality before } UV\ exposur} \times 100\% \quad (1)$$

TABLE 1

Effects of Insecticide Activity of Various Viral Particles After Being Irradiated With UV Light For 90 Min

| Treatment | UV exposure (min) | Mortality (%) ± SEM | OAR (%) ± SEM |
|---|---|---|---|
| NPV | 0 | 89.99 ± 1.925 | 100 ± 2.137 |
| NPV | 90 | 23.33 ± 5.774 | 30.86 ± 10.974 |
| NPV + $SiO_2$ | 90 | 36.66 ± 7.699 | 40.73 ± 8.553 |
| NPV + $SiO_2$ + Green Tea | 90 | 56.66 ± 8.819 | 62.95 ± 9.798 |
| $SiO_2$ | 90 | 6.66 ± 3.848 | 7.40 ± 4.275 |
| NPV + Green Tea | 90 | 31.10 ± 5.553 | 34.56 ± 6.173 |
| GreenTea | 90 | 7.77 ± 2.223 | 8.64 ± 2.470 |
| NPV + $TiO_2$ | 90 | 48.88 ± 2.223 | 54.31 ± 2.467 |
| $TiO_2$ | 90 | 12.22 ± 1.110 | 16.04 ± 2.467 |
| NPV + Lignin | 90 | 49.99 ± 1.925 | 55.55 ± 2.136 |
| Lignin | 90 | 12.21 ± 4.443 | 13.57 ± 4.937 |
| NPV + Gelatin | 90 | 7.77 ± 1.113 | 8.63 ± 1.237 |
| Gelatin | 90 | 6.66 ± 0.000 | 7.40 ± 0.000 |

TABLE 2

Effects of Insecticide Activity of Various Viral Particles After Being Irradiated With UV Light For 180 Min

| Treatment | UV exposure (min) | Mortality (%) ± SEM | OAR (%) ± SEM |
|---|---|---|---|
| NPV | 0 | 81.10 ± 4.005 | 100 ± 4.936 |
| NPV | 180 | 7.77 ± 4.841 | 9.58 ± 5.969 |
| NPV + $SiO_2$ | 180 | 26.66 ± 3.333 | 32.87 ± 4.110 |
| NPV + $SiO_2$ + Green Tea | 180 | 47.77 ± 4.841 | 58.90 ± 5.972 |
| $SiO_2$ | 180 | 6.66 ± 1.925 | 8.21 ± 2.373 |
| NPV + Green Tea | 180 | 16.66 ± 5.090 | 20.54 ± 6.278 |
| Green Tea | 180 | 6.66 ± 5.090 | 8.21 ± 6.276 |
| NPV + $TiO_2$ | 180 | 42.22 ± 4.844 | 52.05 ± 5.972 |
| $TiO_2$ | 180 | 4.44 ± 1.110 | 5.47 ± 1.370 |
| NPV + Lignin | 180 | 29.99 ± 5.093 | 36.98 ± 6.278 |
| Lignin | 180 | 13.32 ± 3.333 | 16.43 ± 4.110 |
| NPV + Gelatin | 180 | 18.88 ± 2.223 | 23.28 ± 2.740 |
| Gelatin | 180 | 6.66 ± 1.925 | 8.21 ± 2.373 |

It is evident from results presented in tables 1 and 2, about 60% of the infectious activity of the gelatin/silica viral particles of the present invention (i.e., NPVs+$SiO_2$+green tea) still remained after UV irradiation; whereas the non-coated NPVs had merely 10% activity remained. Titanium oxide, as well as lignin; respectively provide UV shielding effects to NPVs, however, either substance is still not as effective as the combination of gelatin/silica and green tea extract employed in the viral particles of the present invention.

Taken together, the results from the above study confirmed that the gelatin/silica viral particles manufactured in accordance with the method of this invention may withstand long term UV or sun exposure, and therefore provides improved shelf life over that of a conventional insect virus, and is capable of controlling insect pests susceptible of infection at a more cost effective manner.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of producing a UV-resistant gelatin/silica coated viral particle comprising,
   mixing a gelatin solution with a viral solution to form a mixture;
   adding a silica solution into the mixture to form a precipitate, wherein the silica solution has a pH value of 5.0;
   immersing the precipitate into a green tea extract for at least 30 min so that the green tea extract is absorbed by the precipitate and thereby forming the gelatin/silica coated viral particle.

2. The method of claim 1, wherein the viral solution is produced by suspending a baculovirus in an aqueous solution with a final concentration between about $1\times10^6$ PIB/ml to about $1\times10^9$ PIB/ml.

3. The method of claim 2, wherein the baculovirus is any of a nuclearpolyhedronvirus (NPV), a granulosis virus (GV) or a non-occluded virus.

4. The method of claim 3, wherein the NPV is any of *Autographica californica* NPV (AcNPV), *Spodoptera litura* (SlNPV) or *Lymantria dispar* (LdMNPV).

5. The method of claim 1, wherein the gelatin solution is produced by mixing 1 part of gelatin with 5 parts of a solvent; and the silica solution is produced by mixing 1 part of silica with 8 parts of a solvent.

6. The method of claim 5, wherein the solvent is water or an isotonic buffer.

7. The method of claim 1, wherein the green tea extract is produced by, simmering or dipping 1 portion of a green tea leaf in 99 portions of boiled water for about 30 min; and filtering out the green tea leaf.

8. A UV-resistant gelatin/silica coated viral particle produced by the method of claim 1 characterized in having
   a baculovirus; and
   a gelatin/silica coating disposed outside the baculovirus;
   wherein the gelatin/silica coating has a porosity of about 1.0-10.0 nm, and further includes a green-tea extract, which is absorbed in the porous structure of the gelatin/silica coating.

9. The UV-resistant gelatin/silica coated viral particle of claim 8, wherein the baculovirus is any of a nuclearpolyhedronvirus (NPV), a granulosis virus (GV) or a non-occluded virus.

10. The UV-resistant gelatin/silica coated viral particle of claim 9, wherein the NPV is any of *Autographica californica* NPV (AcNPV), *Spodoptera litura* (SlNPV) or *Lymantria dispar* (LdMNPV).

11. A method of controlling the population of agricultural pests in an agricultural field comprising applying to the agricultural pests or the agricultural field an effective amount of the UV-resistant gelatin/silica coated viral particle of claim 8.

* * * * *